United States Patent
Moloney et al.

(10) Patent No.: US 11,576,436 B2
(45) Date of Patent: Feb. 14, 2023

(54) ELECTRONIC AEROSOL PROVISION SYSTEM

(71) Applicant: NICOVENTURES HOLDINGS LIMITED, London (GB)

(72) Inventors: Patrick Moloney, London (GB); Helmut Buchberger, London (GB)

(73) Assignee: Nicoventures Trading Limited, London (GB)

( * ) Notice: Subject to any disclaimer, the term of this patent is extended or adjusted under 35 U.S.C. 154(b) by 28 days.

(21) Appl. No.: 16/619,670

(22) PCT Filed: Jun. 6, 2018

(86) PCT No.: PCT/GB2018/051540
§ 371 (c)(1),
(2) Date: Dec. 5, 2019

(87) PCT Pub. No.: WO2018/224823
PCT Pub. Date: Dec. 13, 2018

(65) Prior Publication Data
US 2020/0163387 A1   May 28, 2020

(30) Foreign Application Priority Data
Jun. 9, 2017   (GB) ...................... 1709201

(51) Int. Cl.
A24F 40/50   (2020.01)
A24F 40/10   (2020.01)
A24F 40/60   (2020.01)

(52) U.S. Cl.
CPC .............. *A24F 40/50* (2020.01); *A24F 40/10* (2020.01); *A24F 40/60* (2020.01)

(58) Field of Classification Search
CPC .... A61M 15/06; A61M 15/0066; A24F 40/50
See application file for complete search history.

(56) References Cited

U.S. PATENT DOCUMENTS

| | | | |
|---|---|---|---|
| 4,358,665 A | 11/1982 | Owen | |
| 4,523,084 A | 6/1985 | Tamura et al. | |
| 4,947,874 A | 8/1990 | Brooks et al. | |

(Continued)

FOREIGN PATENT DOCUMENTS

| | | | |
|---|---|---|---|
| CN | 1500546 A | 6/2004 | |
| CN | 101522244 A | 9/2009 | |

(Continued)

OTHER PUBLICATIONS

International Search Report and Written Opinion, Application No. PCT/GB2018/051540, dated Sep. 13, 2018, 7 pages.

(Continued)

*Primary Examiner* — Anthony Calandra
(74) *Attorney, Agent, or Firm* — Patterson Thuente, P.A.

(57) ABSTRACT

An electronic vapor provision system includes a vaporizer for vaporizing liquid for inhalation by a user of the electronic vapor provision system; a power supply for supplying power to the vaporizer to vaporize the liquid in response to a user activation of the device; and a control unit configured to estimate a user's expected activation duration and cause power to be supplied to the vaporizer for a period of time shorter than a user's activation duration.

16 Claims, 4 Drawing Sheets

(56) References Cited

U.S. PATENT DOCUMENTS

| | | | |
|---|---|---|---|
| 5,095,921 | A | 3/1992 | Losee et al. |
| 5,372,148 | A | 12/1994 | McCafferty et al. |
| 5,434,386 | A | 7/1995 | Glenn et al. |
| 5,894,841 | A | 4/1999 | Voges |
| 6,766,220 | B2 | 7/2004 | McRae et al. |
| 7,147,170 | B2 | 12/2006 | Nguyen et al. |
| 8,079,371 | B2 | 12/2011 | Robinson et al. |
| 8,511,318 | B2* | 8/2013 | Hon ..................... A24B 15/167 |
| | | | 131/273 |
| 2003/0205229 | A1* | 11/2003 | Crockford ......... A61M 15/0088 |
| | | | 128/204.23 |
| 2004/0081624 | A1 | 4/2004 | Nguyen et al. |
| 2005/0274193 | A1 | 12/2005 | Kwon et al. |
| 2006/0130860 | A1 | 6/2006 | Cholet |
| 2007/0045288 | A1 | 3/2007 | Nelson |
| 2007/0074734 | A1 | 4/2007 | Braunshteyn |
| 2007/0113665 | A1 | 5/2007 | Johnson |
| 2009/0095312 | A1 | 4/2009 | Herbrich et al. |
| 2010/0024517 | A1 | 2/2010 | Ratner |
| 2010/0236546 | A1 | 9/2010 | Yamada et al. |
| 2010/0242974 | A1 | 9/2010 | Pan |
| 2011/0226236 | A1 | 9/2011 | Buchberger |
| 2011/0265806 | A1 | 11/2011 | Alarcon et al. |
| 2012/0048266 | A1 | 3/2012 | Alelov |
| 2012/0199146 | A1 | 8/2012 | Marango |
| 2012/0227752 | A1 | 9/2012 | Alelov |
| 2012/0234821 | A1 | 9/2012 | Shimizu |
| 2012/0242974 | A1 | 9/2012 | LaValley et al. |
| 2012/0298220 | A1 | 11/2012 | Hidaka et al. |
| 2013/0319440 | A1* | 12/2013 | Capuano ............... A61M 15/06 |
| | | | 131/329 |
| 2014/0278258 | A1 | 9/2014 | Shafter |
| 2014/0299125 | A1 | 10/2014 | Buchberger |
| 2015/0136153 | A1 | 5/2015 | Lord |
| 2015/0142387 | A1 | 5/2015 | Alarcon |
| 2015/0245660 | A1 | 9/2015 | Lord |
| 2015/0257448 | A1 | 9/2015 | Lord |
| 2016/0206003 | A1 | 7/2016 | Yamada |
| 2016/0242466 | A1 | 8/2016 | Lord |
| 2017/0035114 | A1 | 2/2017 | Lord |
| 2017/0238596 | A1* | 8/2017 | Matsumoto ............. A24F 40/65 |
| 2017/0368273 | A1* | 12/2017 | Rubin .................. A61M 11/005 |
| 2020/0154770 | A1 | 5/2020 | Hepworth et al. |

FOREIGN PATENT DOCUMENTS

| | | |
|---|---|---|
| CN | 101524187 A | 9/2009 |
| CN | 100566769 C | 12/2009 |
| CN | 201830899 U | 5/2011 |
| CN | 102322893 A | 1/2012 |
| CN | 104544570 A | 4/2015 |
| EP | 0430559 A2 | 6/1991 |
| EP | 1785711 A2 | 5/2007 |
| EP | 1989946 A1 | 11/2008 |
| EP | 2047880 A1 | 4/2009 |
| EP | 2119375 A1 | 11/2009 |
| EP | 2340730 A1 | 7/2011 |
| EP | 2468118 A1 | 6/2012 |
| EP | 2908673 A2 | 8/2015 |
| GB | 2507102 B | 12/2015 |
| JP | S5640917 A | 4/1981 |
| JP | H02124082 A | 5/1990 |
| JP | H069233 U | 2/1994 |
| JP | H08511966 A | 12/1996 |
| JP | H11002577 | 1/1999 |
| JP | 2000132654 A | 5/2000 |
| JP | 3392138 B2 | 3/2003 |
| JP | 2004177579 A | 6/2004 |
| JP | 2005538159 A | 12/2005 |
| JP | 2007192802 A | 8/2007 |
| JP | 2008165769 A | 7/2008 |
| JP | 2009525746 A | 7/2009 |
| JP | 2010526553 A | 8/2010 |
| JP | 2012506263 A | 3/2012 |
| JP | 4933046 B2 | 5/2012 |
| JP | 2012135299 A | 7/2012 |
| JP | 5041550 B2 | 10/2012 |
| JP | 2013524835 A | 6/2013 |
| JP | 2014501106 A | 1/2014 |
| JP | 2014504886 A | 2/2014 |
| JP | 2015537195 A | 12/2015 |
| KR | 20120089544 A | 8/2012 |
| RU | 107026 U1 | 8/2011 |
| WO | WO-03095005 A1 | 11/2003 |
| WO | WO-2007091181 A2 | 8/2007 |
| WO | WO-2009069518 A1 | 6/2009 |
| WO | WO-2010045670 A1 | 4/2010 |
| WO | WO-2011067877 A1 | 6/2011 |
| WO | WO-2011137453 A2 | 11/2011 |
| WO | WO-2012109371 A2 | 8/2012 |
| WO | WO-2015112750 A1 | 7/2015 |
| WO | WO2015131991 | 9/2015 |
| WO | WO2015189556 | 12/2015 |
| WO | WO2016020675 | 2/2016 |
| WO | WO2017055793 | 4/2017 |

OTHER PUBLICATIONS

Akbar et al., "Temperature compensation of piezoresistive pressure sensors" Sensors and Actuators A, vol. 33, 1992, 8 pages.

Extended Search Report dated Jun. 24, 2019 for European Application No. 19164911.0, 8 pages.

Freescale semiconductor, 100 kPa on-chip temperature compensated and calibrated silicon pressure sensors, 10 pages.

Freescale semiconductor, integrated silicon pressure sensor on-chip signal conditioned, temperature compensated and calibrated, 18 pages.

Freescale semiconductor, temperature compensation methods for the Motorola X-ducer pressure sensor element, 11 pages.

International Preliminary Report on Patentability for Application No. PCT/EP2013/071069, dated Apr. 28, 2015,13 pages.

International Preliminary Reporton Patentability for Application No. PCT/GB2017/050781, dated Feb. 27, 2018, 13 pages.

International Preliminary Report on Patentability for Application No. PCT/GB2018/051540, dated 19, Sep. 2019, 11 pages.

International Search Report and Written Opinion for Application No. PCT/GB2017/050781 dated Jun. 14, 2017.

International Search Report for Application No. PCT/EP2013/071069, dated Dec. 20, 2013, 3 pages.

Lu Y., et al., "Photonic Crystal Based All-Optical Pressure Sensor," 2011, pp. 621-623.

Mozek et al., "Digital Temperature Compensation of Capacitive Pressure Sensors" Informacije, vol. 40, 2010.

Notice of Opposition dated Feb. 19, 2020 for European Application No. 13774188.0, 95 pages.

Office Action for Japanese Application No. 2018-086172, dated Dec. 8, 2020, 5 pages.

Office Action dated Feb. 3, 2020 for Japanese Application No. 2018-086172, 17 pages.

Office Action dated Mar. 15, 2016 for Japanese Patent Application No. 2015-537195, 2 pages.

Office Action dated Oct. 17, 2016 for Korean Application No. 10-2015-7010071, 13 pages.

Office Action dated Jul. 24, 2019 for Korean Application No. 10-2018-7035809, 22 pages.

Office Action dated Sep. 26, 2016 for Chinese Application No. 201380054420.1 , 8 pages.

Search Report for Chinese Application No. 201910151850.4 dated Apr. 28, 2021, 2 pages.

Search Report dated Aug. 23, 2017 for Japanese Application No. 2016-227701, 26 pages (40 pages with translation).

Search Report dated Jul. 26, 2016, and Decision to Grant dated Aug. 24, 2016, for Russian Application No. 2015114090, 14 pages.

Second Office Action for Chinese Application No. 201710348338.X, dated Mar. 25, 2020, 17 pages.

Second Office Action and Supplemental Search dated Jun. 19, 2017 for Chinese Application No. 201380054420.1.

(56) References Cited

OTHER PUBLICATIONS

Silicon Microstructures, Active Temperature Compensation and Calibration for MEMS pressure sensors with constant voltage, 6 pages.

* cited by examiner

ELECTRONIC AEROSOL PROVISION SYSTEM

PRIORITY CLAIM

The present application is a National Phase entry of PCT Application No. PCT/GB2018/051540, filed Jun. 6, 2018, which claims priority from GB Patent Application No. 1709201.6, filed Jun. 9, 2017, which is hereby fully incorporated herein by reference.

FIELD

The present disclosure relates to electronic aerosol provision systems such as nicotine delivery systems (e.g. electronic cigarettes and the like).

BACKGROUND

Electronic aerosol provision systems such as electronic cigarettes (e-cigarettes) generally contain a reservoir of a source liquid containing a formulation, typically including nicotine, from which an aerosol is generated, e.g. through heat vaporization. An aerosol source for an aerosol provision system may thus comprise a heater having a heating element arranged to receive source liquid from the reservoir, for example through wicking/capillary action. While a user inhales on the device, electrical power is supplied to the heating element to vaporize source liquid in the vicinity of the heating element to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Usually an electric current is supplied to the heater when a user is drawing/puffing on the device. Typically, the electric current is supplied to the heater, e.g. resistance heating element, in response to either the activation of an airflow sensor along the flow path as the user inhales/draw/puffs or in response to the activation of a button by the user. The heat generated by the heating element is used to vaporize a formulation. The released vapor mixes with air drawn through the device by the puffing consumer and forms an aerosol. When the user has finished the puff (drop of air flow/drop of pressure) the flow or pressure sensor deactivates the electric heater by cutting off the electric current. At that point of time the heater is still at an elevated temperature capable of vaporizing a certain portion of liquid. The heat for this continued vaporization originates from the heat capacity of the heater itself. Subsequently, the heater cools down. When the temperature of the heater falls below the boiling point of the higher volatile formulation components (e.g. water, propylene glycol), the vaporization process stalls. The vapor released during the continued vaporization phase after deactivation is not delivered to the consumer since there is no air flow through the device anymore. Instead the vapor condenses on internal walls of the device causing potential problems (e.g. clogging). The evaporation heat released by the heater during the continued vaporization phase can also be considered as an energy loss. The energy is lost as condensation heat which in turn is heating up structural components of the device. This issue is exacerbated in devices with larger heater elements.

Various approaches are described which seek to help address some of these issues.

SUMMARY

According to a first aspect of certain embodiments there is provided an electronic vapor provision system comprising a vaporizer for vaporizing liquid for inhalation by a user of the electronic vapor provision system, a power supply for supplying power to the vaporizer to vaporize the liquid in response to a user activation of the device, and a control unit configured to firstly learn a user's expected puff duration and secondly cause power to be supplied to the vaporizer for a period of time shorter than a user's expected puff duration.

The control unit continuously measures the puff duration of a given user, and computes an expected puff duration for that user. After activation of the device by the user, the control unit supplies an electric current to the heater for a total period slightly shorter than the expected puff duration (e.g. 0.05-0.5 seconds shorter). Hence the consumer is most likely still puffing on the device when the supply of electric current has already been cut off. As a result the vapor released during the post-deactivation continued vaporization phase (i.e. when no power is supplied to the heater but it is still of a sufficient temperature to vaporize the liquid) can be utilized to form an aerosol inhalable by the consumer. This vapor fraction and the energy used to release it cannot be considered as a loss anymore. That way the energy efficiency and the number of puffs achievable with a given battery capacity can be increased.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used but this term may be used interchangeably with aerosol (vapor) provision system.

Figure 1:
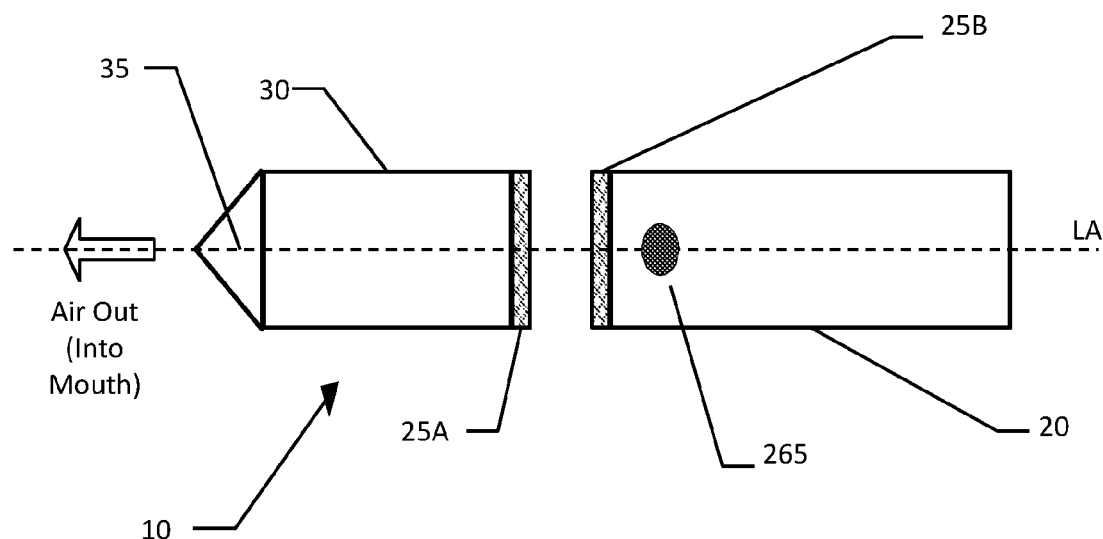
FIG. 1 is a schematic (exploded) diagram of an electronic vapor provision system such as an e-cigarette in accordance with some embodiments of the disclosure.

FIG. 1 is a schematic diagram of an electronic vapor provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer includes an internal chamber containing a reservoir of a payload such as for example nicotine, a vaporizer (such as a heater), and a mouthpiece 35. References to "nicotine" hereafter will be understood to be merely exemplary and can be substituted with any suitable payload. The reservoir may be a foam matrix or any other structure for retaining the nicotine until such time that it is required to be delivered to the vaporizer. The vaporizer is for vaporizing the nicotine, and the cartomizer 30 may further include a wick or similar facility to transport a small amount of nicotine from the reservoir to a vaporizing location on or adjacent the vaporizer. In the following, a heater is used as a specific example of a vaporizer. However, it will be appreciated that other forms of vaporizer (for example, those which utilize ultrasonic waves) could also be used.

The body 20 includes a re-chargeable cell or battery to provide power to the e-cigarette 10 and a circuit board for generally controlling the e-cigarette. When the heater receives power from the battery, as controlled by the circuit board, the heater vaporizes the nicotine and this vapor is then inhaled by a user through the mouthpiece 35. In some specific embodiments the body is further provided with a manual activation device 265, e.g. a button, switch, or touch sensor located on the outside of the body.

The body 20 and cartomizer 30 may be detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device may be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlets. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. When the heater is activated to vaporize the nicotine from the cartridge, the airflow passes through, and combines with, the nicotine vapor, and this combination of airflow and nicotine vapor then passes out of the mouthpiece 35 to be inhaled by a user. Except in single-use devices, the cartomizer 30 may be detached from the body 20 and disposed of when the supply of nicotine is exhausted (and replaced with another cartomizer if so desired). It will be appreciated that the e-cigarette 10 shown in FIG. 1 is presented by way of example, and various other implementations can be adopted. For example, in some embodiments, the cartomizer 30 is provided as two separable components, namely a cartridge comprising the nicotine reservoir and mouthpiece (which can be replaced when the nicotine from the reservoir is exhausted), and a vaporizer comprising a heater (which is generally retained). As another example, the charging facility may connect to an additional or alternative power source, such as a car cigarette lighter.

Figure 2:
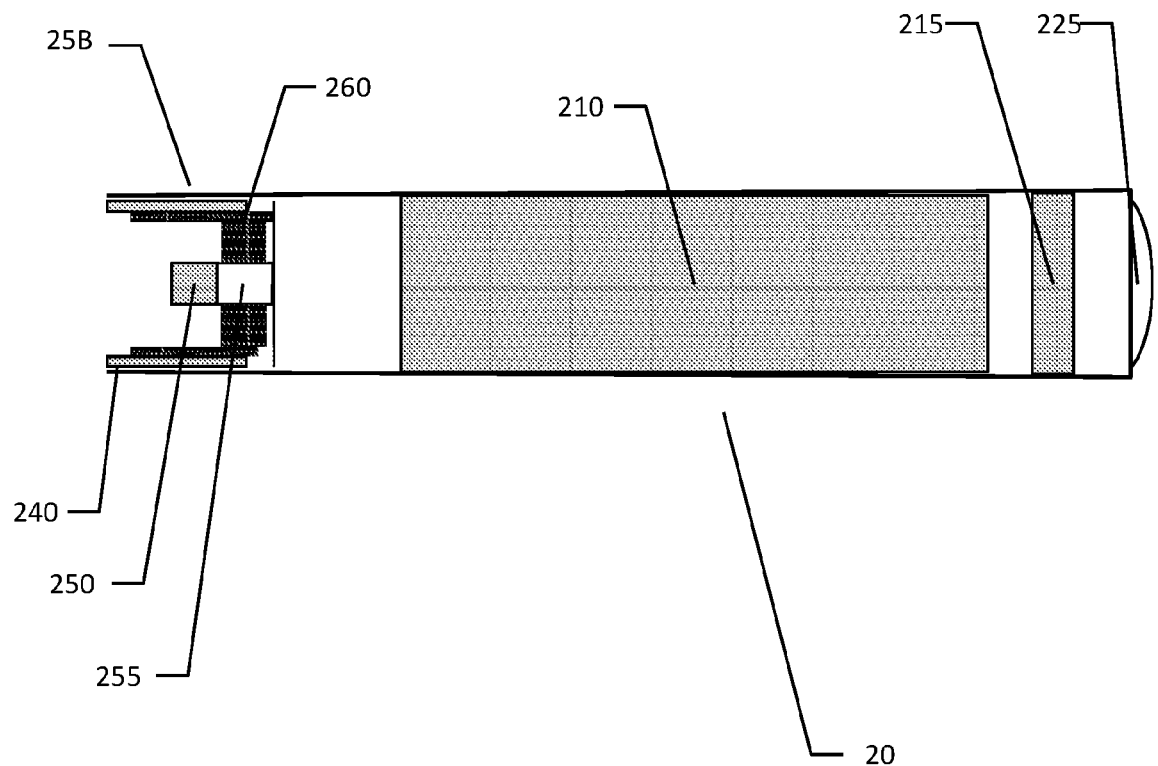
FIG. 2 is a schematic diagram of the body of the e-cigarette of FIG. 1 in accordance with some embodiments of the disclosure.

FIG. 2 is a schematic (simplified) diagram of the body 20 of the e-cigarette 10 of FIG. 1 in accordance with some embodiments of the disclosure. FIG. 2 can generally be regarded as a cross-section in a plane through the longitudinal axis LA of the e-cigarette 10. Note that various components and details of the body, e.g. such as wiring and more complex shaping, have been omitted from FIG. 2 for reasons of clarity.

The body 20 includes a battery or cell 210 for powering the e-cigarette 10 in response to a user activation of the device. Additionally, the body 20 includes a control unit (not shown in FIG. 2), for example a chip such as an application specific integrated circuit (ASIC) or microcontroller, for controlling the e-cigarette 10. The microcontroller or ASIC includes a CPU or micro-processor. The operations of the CPU and other electronic components are generally controlled at least in part by software programs running on the CPU (or other component). Such software programs may be stored in non-volatile memory, such as ROM, which can be integrated into the microcontroller itself, or provided as a separate component. The CPU may access the ROM to load and execute individual software programs as and when required. The microcontroller also contains appropriate communications interfaces (and control software) for communicating as appropriate with other devices in the body 10.

The control unit is operable to learn a user's expected puff duration, and to cause power to be supplied to the vaporizer for a period of time shorter than the user's expected puff duration. As such, the control unit is operable to measure the length of time the user activates the device (i.e. the puff duration). Furthermore the control unit is able to store the length of time of successive puffs in the memory associated with the ASIC. The control unit may utilize the CPU to execute software programs to analyze the puff information.

In some embodiments the CPU analyses the puff information to learn an average puff duration for a user, by calculating the cumulative total duration of all puffs and dividing it by the total number of puffs. In one embodiment the total number of puffs may be limited to a certain number of puffs N, for example up to the last 100 puffs or up to the last 10 puffs. As such, the e-cigarette may be deemed responsive to changes in usage behavior. It will be appreciated that for 'new' devices the user will have taken a limited number of puffs which may be less than the total number typically used to calculate an average. For such devices the total number of puffs taken will be used to calculate an average, while this number is less than the limit. Optionally, given that the memory may be used in a first-in-first out configuration (i.e. a circular configuration) to store the last N puff durations, the memory may be provided with N instances of an average puff duration pre-loaded at manufacture so that the system does not have to operate differently during initial use. Over time, these pre-loaded values are supplanted by measured values from the user. In some other embodiments the control unit learns a user's expected puff duration by employing machine learning. The CPU may be operable to employ certain software to analyze puff information, and identify trends in the user's usage behavior. This may also be more responsive to a user's changing demands.

As noted above, the control unit is operable to cause power to be supplied to the vaporizer for a period of time shorter than the user's expected puff duration. Hence the user is most likely still puffing on the device when the supply of electric current has already been cut off. When the supply of electric current has been cut off, the heater remains at a sufficient temperature to continue to vaporize liquid for a short period of time. By causing the power to be cut off while the user is still puffing on the device, the vapor released during the continued vaporization phase (i.e. when no power is supplied to the heater but it is still of a sufficient temperature to vaporize the liquid) can be utilized to form an aerosol inhalable by the user. This vapor fraction and the energy used to release it cannot be considered as a loss anymore. That way the energy efficiency and the number of puffs achievable with a given battery capacity can be increased. The power to the heater is cut off after being active for a time slightly shorter than the learned user puff duration. In some embodiments, the time power is supplied to the heater is between 0.05 to 0.5 seconds shorter than the expected user puff duration. In one embodiment, the time power is supplied to the heater is 0.3 seconds shorter than the expected user puff duration. More generally, the manufacturer of a device may measure the time taken for a heating element to drop below the vaporization temperature of the payload liquid, and use this time (or a suitable approximation thereto) as the advance cut-off time. Where different available payloads have different vaporization temperatures, then optionally the lowest temperature (the longest advance time) may be chosen, or optionally the device may be adapted to recognize the payload type and select the appropriate cut-off time.

The body 20 further includes a cap 225 to seal and protect the far (distal) end of the e-cigarette 10. Typically there is an air inlet hole provided in or adjacent to the cap 225 to allow air to enter the body 20 when a user inhales on the mouthpiece 35. The control unit or ASIC may be positioned alongside or at one end of the battery 210. In some embodiments, the ASIC is attached to a sensor unit 215 to detect an inhalation on mouthpiece 35 (or alternatively the sensor unit 215 may be provided on the ASIC itself). An air path is provided from the air inlet through the e-cigarette, past the airflow sensor 215 and the heater (in the vaporizer or cartomizer 30), to the mouthpiece 35. Thus when a user inhales on the mouthpiece of the e-cigarette, the CPU detects such inhalation based on information from the airflow sensor 215.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, may be located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
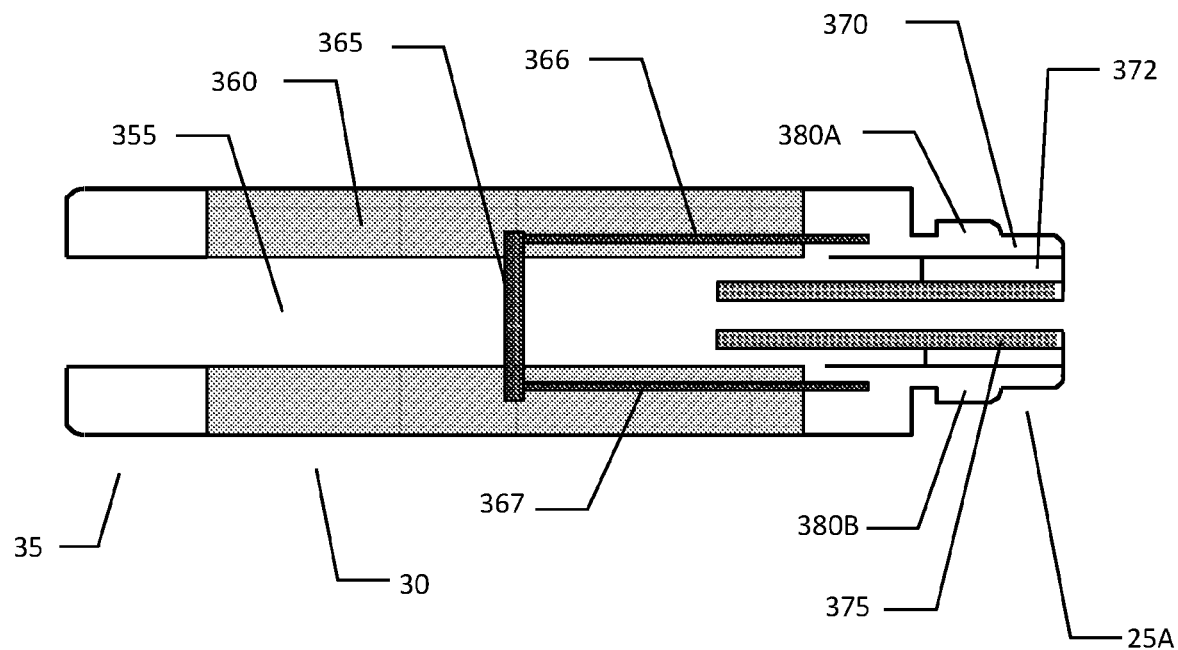
FIG. 3 is a schematic diagram of the vaporizer portion of the e-cigarette of FIG. 1 in accordance with some embodiments of the disclosure.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of nicotine 360 is provided around the air passage 335. This reservoir 360 may be implemented, for example, by providing cotton or foam soaked in nicotine. The cartomizer 30 also includes a heater 365 for heating nicotine from reservoir 360 to generate nicotine vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material.

When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer and body are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
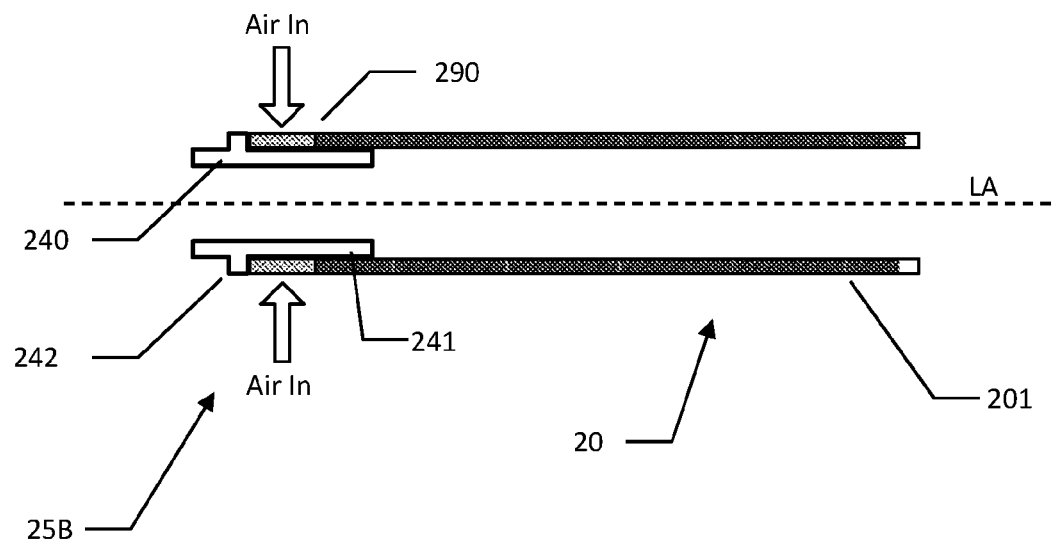
FIG. 4 is a schematic diagram showing certain aspects of one end of the body portion of the e-cigarette of FIG. 1 in accordance with some embodiments of the disclosure.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow when a user inhales on the mouthpiece 35. However, in some embodiments the majority of air that enters the device when a user inhales flows through collar 290 and body connector 240 as indicated by the two arrows in FIG. 4.

Figure 5:
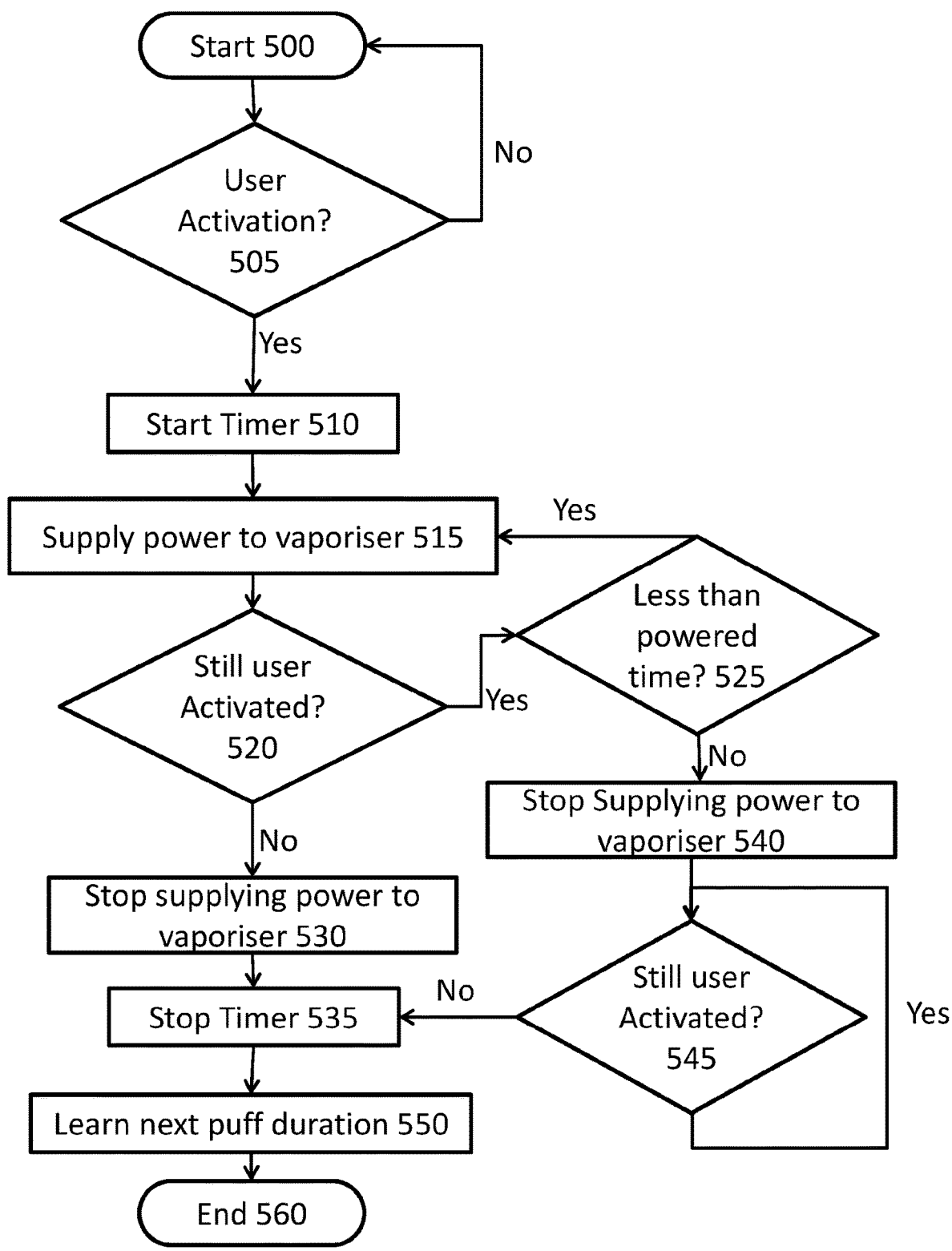
FIG. 5 is a schematic flowchart which illustrates certain aspects of operation of the e-cigarette of FIG. 1 in accordance with some embodiments of the disclosure.

FIG. 5 shows a flow chart illustrating a process performed by the control unit for controlling operation of the electronic vapor provision system according to some embodiments of the present disclosure.

The process starts at 500. At 505, it is determined whether or not the device has been activated by the user. Activation may be by inhalation, button press or touch sensor interaction, for example. If the device has not been activated, then the process returns to the beginning of 505. On the other hand, if the device has been activated, then the process moves onto 510, and a timer is started to measure the total length of time the user activates the device. Immediately after, at 515, the control unit causes power to be supplied to the vaporizer (such as heater 365). This activates the vaporizer and causes the liquid of the cartomizer 30 to be vaporized for inhalation by the user.

The process then moves onto 520, in which it is determined whether or not the device is still being activated by the user, i.e. if the user is still inhaling, pressing the button or interacting with the touch sensor, as applicable. If it is determined at 520 that the device is still activated, then the process moves onto 525. At 525, the control unit compares the current time against the first period of time (i.e. the period of time shorter than the expected puff duration, that the control unit powers the vaporizer). If the current time is less than the first period of time then the system returns to 515 and continues to supply power to the vaporizer. A loop is formed by 515, 520, and 525 that can only be broken by the user deactivating the device at 520 or if the period of activation exceeds the first period of time, at 525. If the user deactivates the device, the system proceeds to 530 and immediately stops supplying power to the vaporizer. Alternatively, if the period of activation exceeds the first period of time the system proceeds to 540 and immediately stops supplying power to the vaporizer.

Figure 6:
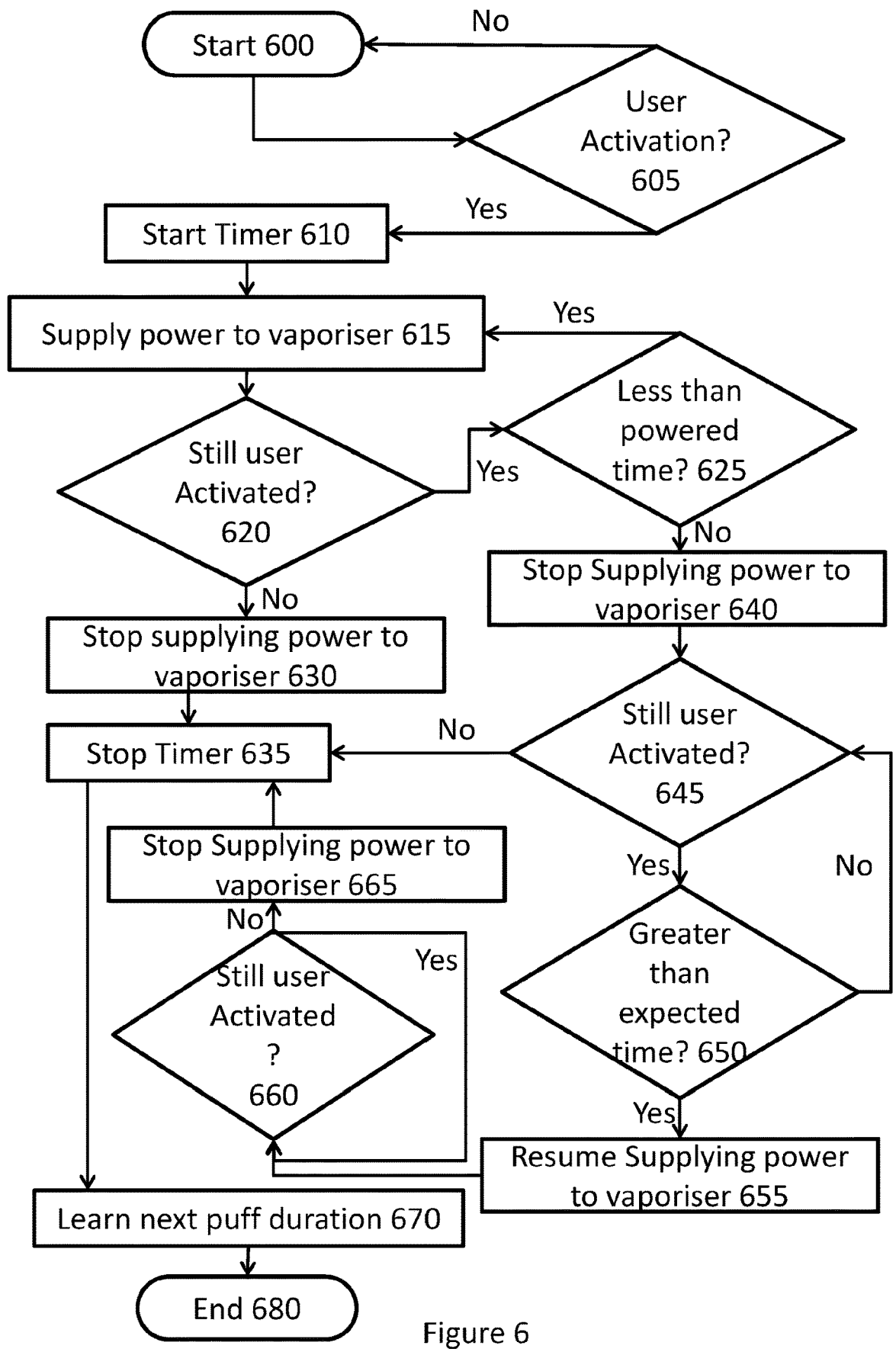
FIG. 6 is a schematic flowchart which illustrates certain aspects of operation of the e-cigarette of FIG. 1 in accordance with some other embodiments of the disclosure.

After 530 the control unit can immediately stop the timer at 535, so that the time measured corresponds to the length of time the device has been activated. Alternatively, after 540, power has stopped being supplied to the vaporizer but the user is still activating the device, e.g. still puffing. As such, 545 continuously queries whether the user has ceased to activate the device. Once the user has stopped, the system proceeds to 535 and the timer is stopped, so that the time measured corresponds to the length of time the device has been activated. At 550 the control unit incorporates the latest puff duration into the analysis of the expected puff duration, to estimate the user's next expected puff duration. The process ends at 560 and returns the device to 500, ready for the next user activation. Note that although FIG. 6 shows starting of the timer 510 and supplying power to the vaporizer 515 being performed sequentially, in practice these may be performed in parallel.

In an embodiment, the first period of time is 0.3 seconds shorter than the expected puff duration of the user. It is expected that 0.3 seconds represents a threshold time at which a user cannot detect the heater has switched off prematurely. As an example, for an expected puff duration of 3 seconds the first period of time would be 2.7 seconds. If the user presses an activation button for 2.9 seconds then 0.2 seconds of energy have been saved. Given the short period of time and the thermal inertia of the heater, liquid vaporized in this time is inhaled while no power is wasted. Furthermore as less liquid is vaporized as the temperature of the heater drops, once the user stops inhaling there will be less additional vaporization that subsequently condenses on the internal walls of the device.

Thus, it can be seen from FIG. 5 that power is provided to the vaporizer for a period of time slightly shorter than the expected puff duration of the user, unless the user prematurely stops the puff after a time much shorter than the expected puff duration. In general terms, the vaporizer remains activated, thus vaporizing the liquid, for as long as necessary so that the user does not detect a reduction in quality. This mechanism is hidden from the user and, therefore, does not require the user to practice certain behavior in relation to the use of the device; for example releasing a button 265 early to deactivate the device prior to finishing the puff. Instead this functionality is inherent in the device, to provide a more intuitive experience.

However, the embodiment detailed in FIG. 5 has the potential, in some circumstances, to provide an unsatisfactory user experience. If the actual user puff duration exceeds the estimated (expected) user puff duration greatly, then the user may detect a significant loss of performance in the final stage of the puff. To overcome this issue some embodiments of the device are further configured to resume supplying power to the vaporizer, in response to a longer than expected puff, for a second period of time.

FIG. 6 shows a flow chart illustrating a process performed by the control unit for controlling operation of the electronic vapor provision system according to some embodiments of the present disclosure, wherein the system is further configured to resume supplying power to the vaporizer in response to a longer than expected puff.

The process starts at 600. At 605, it is determined whether or not the device has been activated by the user (again for example by inhalation, button press or touch sensor interaction). If the device has not been activated, then the process returns to the beginning of 605. On the other hand, if the device has been activated, then the process moves to 610, and a timer is started to measure the total length of time the user activates the device. Immediately after, at 615, the control unit causes power to be supplied to the vaporizer (such as heater 365). This activates the vaporizer and causes the liquid of the cartomizer 30 to be vaporized for inhalation by the user.

The process then moves onto 620, in which it is determined whether or not the device is still being activated by the user. If it is determined at 620 that the device is still activated, then the process moves onto step 625. At 625, the control unit compares the current time against the first period of time (i.e. the period of time shorter than the expected puff duration that the control unit powers the vaporizer). If the current time is less than the first period of time then the system returns to 615 and continues to supply power to the vaporizer. A loop is formed by 615, 620, and 625 that can only be broken by the user deactivating the device at 620 or the period of activation exceeding the first period of time, at 625. If the user deactivates the device, the system proceeds to 630 and immediately stops supplying power to the vaporizer. Alternatively, if the period of activation exceeds the first period of time the system proceeds to 640 and immediately stops supplying power to the vaporizer.

After 630 the control unit can immediately stop the timer at 635, so that the time measured corresponds to the length of time the device has been activated. Alternatively, after 640, power has stopped being supplied to the vaporizer but the user is still activating the device, i.e. still puffing. As such, 645 queries whether the user has ceased to activate the device. If the user is not activating the device, the control unit proceeds to 635 and the timer is stopped, so that the time measured corresponds to the length of time the device has been activated. If the user is still activating the device, the control unit proceeds to 650 and the control unit queries whether the current time is greater than the expected puff duration. If the current time is not greater, the system loops back to 645. If, however the current time is greater, the system proceeds to 655 and the control unit resumes supplying power to the vaporizer. At 660 the system continuously queries whether the user has ceased to activate the device. Once the answer is no the system proceeds to 665 and the control unit stops supplying power to the vaporizer. Next the control unit proceeds to 635 and the timer is stopped, so that the time measured corresponds to the length of time the device has been activated by the user. At 670 the control unit incorporates the latest puff duration into the analysis of the expected puff duration, to estimate the next puff duration. The process ends at 680 and returns the device to 600, ready for the next user activation.

Different embodiments may adopt different approaches to the power management of the heater. The embodiment of FIG. 6 powers the heater for a first period of time, slightly shorter than the expected puff duration, and then resumes powering the heater for a second period of time if the user activation of the device exceeds the expected puff duration. In one embodiment, it may be advantageous to resume powering the heater for the second period of time at a lower power level, thereby reducing the continued vaporization phase after the user deactivates the device. In an alternate embodiment, the power may be pulsed repeatedly during the second period while the user continues to activate the device. For an equivalent period of time, the integrated energy supplied by the pulses will be significantly less than the integrated energy supplied by the power level of the first period of time. In either of these embodiments the energy usage is reduced, enhancing the number of puffs that can be achieved per battery, whilst also ensuring that the performance of the device is not noticeably reduced. Additionally by reducing the length of the continued vaporization phase, there is less condensation of vapor on the internal walls of the device. In certain embodiments, the control unit may not completely stop powering the heater after the first period, and instead may immediately start pulsing power to the heater or may immediately power the heater at a lower power for the second period of time. The thermal inertia of the heater will be slowly reduced; however this will not occur as quickly as if the heater were powered off and therefore if the user activates the device for a larger than expected time they are less likely to notice a loss of performance.

As previously mentioned, some embodiments may adopt implementations of a manual activation device 265. The manual activation device may be activated by the user to cause the control unit to supply power to the vaporizer to vaporize the liquid. In these embodiments the user activation of the manual activation device facilitates the user activation of the device, thereby starting the processes described above, for example in FIG. 5 and FIG. 6. The manual activation device 265 may be, for example, a physical button or switch or may be a touch sensor (such as a resistive or capacitive touch sensor) which is activated simply by being touched by the user. In addition, the method of activating and deactivating the manual activation device 265 may also take a range of different approaches. For example, in some cases the manual activation device may be activated for a predetermined period of time after the button 265 is pressed or touched, after which the manual activation device is de-activated. Such an implementation helps to ensure that the manual activation device is de-activated by the user, although the user does not have full (direct) control over the supply of power to the vaporizer.

In some embodiments, the manual activation device 265 comprises a button which is activated by a first press of the button by the user, and then deactivated by a second (subsequent) press of the button by the user. In other words, alternate presses of the button activate and then deactivate the manual activation device. During the time period between the first and second press, the microcontroller regards the manual activation device 265 as activated. This method has the advantage of providing the user with direct control over the duration of activation, although the manual activation device may remain activated if the user forgets or neglects to make a second press. In another example, the manual activation device 265 is deemed activated for as long as the button is continuously pressed by the user. This method again gives the user control over how long the vaporizer is activated. Moreover, it is natural for a user to stop pressing the button 265 when they have finished using the e-cigarette, so it is unlikely that the manual activation device would remain in an activated state unintentionally.

Similar methods may also be adopted when the manual activation device 265 comprises a touch sensor. That is, in one example, the manual activation device 265 is deemed to be activated following a first touch of the touch sensor by the user and then deemed to be deactivated following a second touch of the touch sensor by the user. During the time period between the first and second touch, the manual activation device 265 is deemed activated. In another example, the manual activation device 265 is deemed activated for as long as the touch sensor is continuously touched by the user.

In another example, if the manual activation device 265 comprises a manual switch, such as a slidable or rotatable switch, then the manual activation device 265 will be activated when the switch is put into an "on" position and deactivated when the switch is put into an "off" position. In such embodiments, the switch may be biased towards the "off" position so that the user has to continually hold the switch in the "on" position in order for the manual activation device to be activated. In this case, when the user stops holding the switch in the "on" position, the switch will automatically return (under the influence of a spring or some other resilient bias mechanism, etc) to the "off" position. This not only makes it more difficult for the switch to be unintentionally retained in the "on" (activated) position, but also makes it easier for the user, since the user does not have to manually change the switch back to the "off" position after inhaling on the e-cigarette.

The manual activation device 265, be it a button, touch sensor, switch or any other suitable device, is generally positioned such that it is easily accessible to the user when the user holds the e-cigarette 10 so as to inhale on it. For example, the manual activation device 265 may be located somewhat closer to the proximal (mouth) end of the e-cigarette than to the distal (cap) end of the e-cigarette, since the user is more likely to hold the e-cigarette closer at a position closer to its proximal end (as is the case for conventional combustible cigarettes). Thus in the example shown in FIG. 1, the button 265 is located on the body portion 25 (since the cartridge 30 is disposable), but at the end nearest to the mouthpiece. The button may be activated (pressed, moved or touched) conveniently while the e-cigarette is being held by a user. While the manual activation devices have been described in-depth with regard to the activation of the device and consequently the vaporizer, it will be appreciated that in many embodiments additional manual activation devices may serve ancillary functions, for example an on/off or lock switch.

In alternate embodiments, an air flow sensor may be implemented in the device so that the user may activate the device and cause the control unit to supply power to the vaporizer to vaporize the liquid by inhaling on the device. In these embodiments the user activation of the air flow sensor facilitates the user activation of the device, thereby starting the processes described above, for example in FIG. 5 and FIG. 6. The body 20 includes the sensor unit 215 located in or adjacent to the air path through the body 20 from the air inlet to the air outlet (to the vaporizer). The sensor unit 215 may include a pressure drop sensor and temperature sensor (also in or adjacent to this air path). It will be appreciated, however, that the sensor unit 215 may include the pressure drop sensor without the temperature sensor or may include an airflow monitor to directly measure airflow (rather than pressure drop). Thus when a user inhales on the mouthpiece of the e-cigarette, the control unit detects such inhalation based on information from the pressure drop sensor. In response to the detection of an inhalation, the CPU supplies power to the heater, which thereby heats and vaporizes the nicotine from the wick for inhalation by the user.

Hence it will be appreciated that "activation" and "deactivation" may equally be considered separate actions (such as pushing a button or switch on and then off) or the commencement and cessation of a single action (such as inhalation, pressing a button or interacting with a touch sensor).

Advantageously, the above described embodiments act to reduce the energy supplied to the heater during each puff. As such, this may increase the number of puffs for a given battery capacity or present an opportunity to reduce the battery capacity of the device. The reduced length of the continued vaporization phase additionally reduces unwanted condensates on the internal walls of the device, improves puff count for a given volume of liquid, and may also help to alleviate carbonyl build up, which occurs when the heater is on but there is no airflow in the device.

Thus, there has been described an electronic vapor provision system comprising a vaporizer for vaporizing liquid for inhalation by a user of the electronic vapor provision system; a power supply for supplying power to the vaporizer to vaporize the liquid in response to a user activation of the device; and a control unit configured to: i) estimate a user's expected activation duration; ii) cause power to be supplied to the vaporizer for a period of time shorter than a user's activation duration. Variations on this system have similarly been described as outlined herein. Likewise, there has been described a method of operating an electronic vapor provision system including a vaporizer for vaporizing liquid for inhalation by a user of the electronic vapor provision system; wherein the electronic vapor provision system includes a power supply for supplying power to the vaporizer to vaporize the liquid in response to a user activation of the device, the method comprising;

i) causing a control unit to estimate a user's expected activation duration; and ii) causing a control unit to supply power to the vaporizer for a period of time shorter than a user's activation duration. Variations on this method have similarly been described as outlined herein.

While the above described embodiments have in some respects focused on some specific example aerosol provision systems, it will be appreciated the same principles can be applied for aerosol provision systems using other technologies. That is to say, the specific manner in which various aspects of the aerosol provision system function are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An electronic vapor provision system comprising:
   a vaporizer for vaporizing liquid for inhalation by a user of the electronic vapor provision system;
   a power supply for supplying power to the vaporizer to vaporize the liquid in response to a user activation of the electronic vapor provision system; and
   a control unit configured to:
      estimate a user's expected activation duration, and
      cause power to be supplied to the vaporizer for a period of time shorter than the user's estimated expected activation duration by between 0.05 seconds and 0.5 seconds; and
      resume causing power to be supplied to the vaporizer for a second period of time, if the user activates the electronic vapor provision system for a duration exceeding the user's expected activation duration, the second period of time ending when the user ceases activation of the electronic vapor provision system.

2. The electronic vapor provision system of claim 1, wherein user activation of the electronic vapor provision system is by one selected from the group consisting of:
   inhalation through the electronic vapor provision system;
   pressing a button; and
   interaction with a touch sensor.

3. The electronic vapor provision system of claim 1, wherein the period of time is shorter than the user's estimated expected activation duration by 0.3 seconds.

4. The electronic vapor provision system of claim 1, wherein the control unit comprises a CPU.

5. The electronic vapor provision system of claim 1, wherein the control unit employs machine learning software to learn the user's expected activation duration.

6. The electronic vapor provision system of claim 1, wherein the control unit learns the user's expected activation duration by:
   measuring the activation duration for a predetermined number of preceding activations of a given user, and
   calculating the user's average activation duration based on the measuring.

7. The electronic vapor provision system of claim 6, wherein the user's average activation duration is calculated using one selected from the group consisting of:
   up to the last 100 activations; and
   up to the last 10 activations.

8. The electronic vapor provision system of claim 1, wherein the control unit provides power at a lower level for the second period of time.

9. The electronic vapor provision system of claim 1, wherein the control unit provides pulses of power for the second period of time.

10. The electronic vapor provision system of claim 1, wherein the control unit is further configured to cause power to be supplied to the vaporizer at a lower power level for a second period of time immediately after the first period of time ends, the second period of time ending when the user ceases activation of the electronic vapor provision system.

11. The electronic vapor provision system of claim 1, wherein the control unit is further configured to cause power to be supplied to the vaporizer in pulses for a second period of time immediately after the first period of time ends, the second period of time ending when the user ceases activation of the electronic vapor provision system.

12. The electronic vapor provision system of claim 1, further comprising a sensor for detecting airflow through the electronic vapor provision system as a result of the inhalation by the user, wherein the sensor provides for user activation of the electronic vapor provision system.

13. The electronic vapor provision system of claim 1, further comprising a manual activation device, wherein the manual activation device provides for user activation of the electronic vapor provision system, the manual activation device comprising one selected from the group consisting of:
   a button; and
   a touch sensor.

14. The electronic vapor provision system of claim 1, wherein the vaporizer is a heater which is supplied with power from the power supply to heat and thereby vaporize the liquid for inhalation by the user.

15. The electronic vapor provision system of claim 1, wherein the liquid comprises nicotine.

16. A method of operating the electronic vapor provision system of claim 1, the method comprising;
   causing the control unit to estimate the user's expected activation duration;
   causing the control unit to supply power to the vaporizer for a period of time shorter than the user's estimated expected activation duration by between 0.05 seconds and 0.5 seconds; and
   causing the control unit to resume causing power to be supplied to the vaporizer for a second period of time, in response to the user activating the electronic vapor provision system for a duration exceeding the user's expected activation duration, the second period of time ending when the user ceases activation of the electronic vapor provision system.

* * * * *